United States Patent
Lind

(10) Patent No.: US 6,530,343 B1
(45) Date of Patent: Mar. 11, 2003

(54) CONTROL OF AMMONIA AND PHOSPHORUS IN MILKING PARLORS

(75) Inventor: Christopher B. Lind, Flanders, NJ (US)

(73) Assignee: General Chemical Corporation, Parsippany, NJ (US)

( * ) Notice: Subject to any disclaimer, the term of this patent is extended or adjusted under 35 U.S.C. 154(b) by 0 days.

(21) Appl. No.: 10/171,501

(22) Filed: Jun. 13, 2002

(51) Int. Cl.7 .................................................. A01J 5/00
(52) U.S. Cl. .................................................... 119/14.03
(58) Field of Search .............................. 119/14.03, 428, 119/432, 436, 437, 444, 447, 450, 527; 424/405, 421, 76.21, 76.5, 76.6, 76.8, 682, 685, 698, 718

(56) References Cited

U.S. PATENT DOCUMENTS

| | | | | |
|---|---|---|---|---|
| 3,029,783 A | * | 4/1962 | Sawyer | |
| 4,028,238 A | * | 6/1977 | Allan | 210/711 |
| 4,034,078 A | * | 7/1977 | Van Horn | 424/76.6 |
| 4,209,335 A | * | 6/1980 | Katayama et al. | 106/645 |
| 4,306,516 A | * | 12/1981 | Currey | 119/171 |
| 5,039,481 A | * | 8/1991 | Pacifici et al. | 422/4 |
| 5,176,879 A | * | 1/1993 | White et al. | 119/171 |
| 5,362,842 A | * | 11/1994 | Graves et al. | 210/732 |
| 5,589,164 A | * | 12/1996 | Cox et al. | 252/175 |
| 5,609,123 A | * | 3/1997 | Luke et al. | 119/173 |
| 5,622,697 A | * | 4/1997 | Moore, Jr. | 119/171 |
| 5,634,431 A | * | 6/1997 | Reddy et al. | 119/173 |
| 5,865,143 A | | 2/1999 | Moore | |
| 5,890,454 A | | 4/1999 | Moore | |
| 5,914,104 A | | 6/1999 | Moore | |
| 6,346,240 B1 | * | 2/2002 | Moore, Jr. | 424/76.6 |

* cited by examiner

Primary Examiner—Thomas Price
(74) Attorney, Agent, or Firm—Arthur J. Plantamura

(57) ABSTRACT

A method of controlling ammonia levels and soluble phosphorus generated from the animal waste in milking parlors comprising applying to the parlor floor an acidic aluminum salt liquid. The treatment effective amount is effective to reduce phosphorus solubility in the manure; reduce phosphorus runoff and/or phosphorus leaching from fields fertilized with manure; inhibit ammonia volatilization from the manure; flocculate solids in the manure; reduce pathogens in the manure; increase the nitrogen content in the manure; and/or reduce acid rain associated with the manure.

9 Claims, No Drawings

CONTROL OF AMMONIA AND PHOSPHORUS IN MILKING PARLORS

FIELD OF THE INVENTION

This invention relates to the control of animal wastes including the control of the ambient environment which develops from animal waste in animal housing enclosures. The invention is particularly applicable to a system for controlling the level of ammonia generated in the atmosphere by animal waste and to a treatment which decreases soluble phosphorus resulting from the animal waste.

BACKGROUND OF THE INVENTION

In the production of milk and dairy products the dairy animals are typically milked in what is termed a milking parlor. This is a confined area where the animals are restrained while being milked either manually or by way of mechanical milking apparatus.

The milking parlors are confined, humid, warm areas. The animals defecate and urinate generating considerable ammonia. The problem is worse in northern climates where heating costs force operators to minimize the circulation of cold, outside air through the parlor space. The concentration of ammonia in such confined spaces can exceed level considered healthy for animals and the workers.

Further, the feces and urine of the animals contain considerable amounts of phosphorus. These wastes are typically flushed or scrape out of the milking parlor and disposed of on land for their fertilizer value. One of the problems with this approach is that the manure in such fertilizer contains neatly equal amounts of phosphorus and nitrogen, but the nutrient requirements for growing plants are 8–15 times higher for nitrogen. The results are an over application of phosphorus and runoff of the unused phosphorus from farming land into the surface waters and eutrophication of the adjacent waterways.

No practical solution is known as being practically applicable to milking parlors for ammonia control other than ventilation. The use of ventilation increases substantially the energy costs in winter; the colder the weather the greater the cost. Accordingly, there is a need for a system that is capable of providing a means to reduce ventilation costs; for controlling control in animal wastes; for reduction of ammonia stress in animals; for vermin control, i.e. from flies that are attracted to the ammonia smell and, also, in a special way, for worker comfort. Additionally, because ammonia is a regulated air pollutant a means to control emissions of ammonia has a positive environmental impact.

SUMMARY OF THE INVENTION

The invention employs acidic salts of aluminum, most preferred aluminum sulfate and aluminum chloride, to scrub the ammonia from the air and to reduce the pH on floors and of droppings to inhibit the volatilization of ammonia. Ammonia can not be formed at pH levels below 6; this acidification of the area will inhibit ammonia formation. Conventional mineral acids like sulfuric or hydrochloric may technically be effective for this use, however, they are far too aggressive to the animals and physical structure to be considered. In addition, the storage and handling of commercial acids requires equipment specifically devised for handling hazardous material and specialized training. Such requirements add substantially to costs.

In accordance with the invention, the alum or other aluminum salts solution is sprayed on the floor. The alum can also be applied at a level of a few inches to a foot above the floor by means of a pumping system. This system can be mechanically driven or the application means (pump) may employ compressed air as the motive force. The spray will, both chemically react with the ammonia to form ammonium sulfate and physically entrap the ammonia in the spray. The spray can be continuous or be activated by ammonia sensors, by timers or manually by using known soluble commercial apparatus for application of this kind.

The phosphorus inactivation of the manure is completed by the chemical reaction of aluminum with the soluble phosphorus contained in the waste. The resulting end product is aluminum phosphate, a compound that is largely insoluble between pH 3 and 9. Being insoluble, it is not available as a nutrient to the algae in surface waters and so can not contribute to eutrophication.

The invention provides especial advantages to dairies in the more northern climates where the more weather tight, more confined, enclosures to insulate against the cold have a pronounced problem with ammonia control in milking parlors. The cost of the system provided by the invention is sufficiently inexpensive to make it a viable alternative to the minimum necessary ventilation needed even in the coldest weather to maintain a tolerable environment in a confined area. Further, in states wherein phosphorus control is an issue, the phosphorus binding aspect of the technology involved in the system of the invention could have economic implications in the farm's nutrient management program by allowing a higher level of manure disposal because of the bound phosphorus.

DESCRIPTION OF THE INVENTION

The present invention may be understood more readily by reference to the following detailed description of the invention and the Examples included herein. With reference to the present compounds, compositions and methods disclosed and described, it is to be understood that the invention is not limited to specific methods or to particular formulations, as such may, of course, vary. It is also understood that the terminology used herein is for the purpose of describing particular embodiments only and, unless the context dictates otherwise, such terminology is not intended to be limiting.

Of the acidic salts of aluminum which are contemplated for use by the invention, the preferred salts are alum and aluminum chloride. The alum or aluminum sulfate referred to in the specification is $Al_2(SO_4)_3 \cdot nH_2O$, or the residue thereof wherein n is generally from about 14 to 18. The aluminum chloride is $AlCl_3 \cdot nH_2O$ or the residue of $AlCl_3 nH_2O$ wherein n is from about 4 to about 8. In a more preferred embodiment the treatment composition comprise aluminum chloride hexahydrate, or the residue thereof.

This invention relates generally to the treatment of animal wastes generated, for example, in a milking parlor, to reduce harmful phosphorus runoff from farming land field to which the milking parlor wastes are applied, and to the reduction of ammonia emitted from the animal waste that is generated in the milking parlor. The invention is particularly applicable to a relatively toxic ammonia atmosphere that is inevitably generated during the confinement of cows in the milking parlors.

Milking parlors generally comprise an animal enclosure including a raised animal rearing platform and a lower manure collection area below the platform and the animal rearing area. The platform has a plurality of openings defined therein permitting manure produced in the animal rearing area to be swept through the platform to the manure collecting area. The rearing facility further contemplates, but is not limited to the incorporation of at least one sprayer nozzle disposed in the manure collection area adjacent an underside surface of the platform. A supply of liquid aluminum sulfate or other aluminum chemical treatment liquid composition is provided which is fluidly connected with the sprayer nozzle or nozzles. The milking parlor facility further comprises means for delivering liquid aluminum from the supply to the sprayer nozzle under pressure.

The liquid delivery arrangement, which preferably comprises a suitable spray means, sprays the liquid alum solution through the sprayer nozzles during appropriately predetermined time intervals (depending on ambient conditions) which are effective to substantially strip the air of any ammonia gas that is present and to deposit a layer of the liquid aluminum treatment on the surface of the manure in the manure collection area to substantially inhibit volatilization of ammonia from the collected manure. This markedly reduces the concentration of ammonia gas in the upper animal rearing level of the facility thereby creating improved health conditions for the animals reared therein as well as for the facility workers involved. The treatment also increases the nitrogen content of the manure by preventing ammonia losses and reduces the quantity of soluble phosphorus present in the manure making the manure more useful as an agricultural fertilizer.

The present invention is thus seen as affording a definite improvement that is useful in enhancing the environment above the manure accumulation during the confinement of livestock in relatively closed spaces. This is effected by periodically spraying the liquid aluminum treating solution onto the manure collection level in an amount sufficient to provide a treated or coated surface on the accumulated manure which maintains the pH of the surface of the manure at a pH of about 7.0 or lower. The liquid solution is sprayed onto an upper surface of the manure in amounts and at spraying intervals to yield a pH at less than or equal to pH of about 7.0. In addition, the liquid aluminum composition is sprayed in amounts and at spraying intervals which are effective to control the atmospheric concentration of ammonia in the animal confinement space at a level of less that or equal to about 25 ppm.

The following system example is presented so as to provide those of ordinary skill in the art with a more complete disclosure and to illustrate how the compounds claimed herein are made and evaluated. The example is intended to be purely exemplary of the invention and the details thereof are not intended to limit the scope of the invention. In the example and description of variables which follows, the effort has been made to ensure accuracy with respect to numbers (e.g., amounts, temperature, etc.). Unless indicated otherwise, parts are parts by weight, temperature is in ° C. or is at room temperature, and pressure is at or near atmospheric.

EXAMPLE

A typical system consists of a commercial tote (325 gallon capacity) of standard liquid alum; a 500 gallon plastic tank with mixer; an air compressor; an alum pump; piping comprising 0.375 inch polyethylene; nozzles; and control system is utilized. The system is activated either manually or automatically by means of a timer and/or ammonia sensor. The pump, sufficiently sized to provide requisite amount of alum to provide a spray of about 1 gallon per minute, or as large as needed depending on size of milking parlor. The nozzles and spray pattern should allow for coverage of 0.1 gallons per square foot up to 25 gallons per square foot depending on size of parlor, number of animals and cleanout frequency. More animals and fewer cleanouts will require larger application rates. To facilitate spray pattern the alum can be injected by compressed air. This is a desirable feature since it will also clean nozzles and reduce crystallization. Also the concentrated commercial 48% aluminum solution can be diluted in half in plastic tank. This reduces viscosity of alum and provide better spraying patter. Dry alum should be mixed to between 10% w/w and 20% w/w to reduce hydrolysis in solutions <10% and slow dissolution in solution >20%. In reality any solution strength ≧0.1% by weight will work—it is a matter of how much water is available and of liquid handling considerations.

Prior to the milking operation a 50% solution, solution of liquid alum (equivalent to a 24% solution of dry alum) is made in the plastic storage tank. When milking commences, the alum pump is activated by signal from a timer controlled by the milking operator. The alum pumps into the lines where air pressure used to force the alum through the nozzles in a spray directed at the floor and areas where the animal wastes are concentrated. If the ammonia builds up the timer can be set for more frequent alum application.

Variables

The use of ammonia sensing devices to activate the system is a desirable feature in freeing the workers in the milking parlors from manually spraying alum. In all cases solutions of aluminum chloride can be substituted for alum with appropriate changes in materials of construction to handle a chloride based product. Partial amounts of iron chloride and iron sulfate such as ferric chloride, ferric sulfate, ferrous chloride and ferrous sulfate and mixtures thereof can be used with the aluminum salt in this application to provide acidification of manure for ammonia control and phosphorus binding. They are not preferred in substantial proportions because of the severe staining of noncompounds on physical structures, animal and workers. Further iron compounds—ferric chlorides and ferrous chlorides especially tend to be more corrosive then alum and may result in an increased level of damage to the milking parlor.

Mixtures of alum and aluminum chloride, polyaluminum chloride, aluminum chlorhydrate, polyaluminum hydroxysulfate or any representative of the family of polyaluminum products or mixtures thereof can be used effectively. Polyelectrolytes can be added to enhance fluid handling characteristics or solids flocculation in the amount of <1% by weight to >20% by weight. Typical polyelectrolytes added to the acidic salt solutions to improve viscosity and assist in solids flocculation are representatives of the families of polyDADMAC's and poly-epichlorohydrin/dimethylamine (pEPI/DMA) with molecular weights ≦25,000 to ≦1,000,000.

The injection and spray system can be sized and configured based on physical constraints, number of animals and milking procedures.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for controlling atmospheric ammonia levels and soluble phosphorous generated from animal waste in milking parlors which include a raised animal rearing platform and a lower manure collection area which comprises providing spray means for automatically dispensing an aluminum salt liquid under pressure onto the parlor platform in an amount sufficient to maintain the pH level at a pH of 7 or lower and an atmospheric concentration of ammonia in the ambient atmosphere at about 25 ppm or less and wherein the aluminum salt is selected from $Al(SO4)_3nH_2$) or the residue thereof, wherein n is from about 14 to about 18; and from $AlCl_3nH_2O$ or $Al(NO_3)_3mH_2O$, or the residue thereof wherein n is from about 4 to 8, and m is from 0 to 12, and wherein said salt is sufficient to control the atmospheric concentration of the atmospheric ammonia in the milking parlor space at a level of about 25 ppm or less.

2. A method according to claim 1 wherein the aluminum salt is aluminum sulfate.

3. A method according to claim 1 wherein the aluminum salt is aluminum chloride.

4. The method of claim 1 wherein the acidic aluminum salt comprises a mixture of aluminum sulfate and aluminum chloride.

5. The method of claim 1 wherein the acidic aluminum salt comprises a mixture of aluminum sulfate and a polyelectrolyte.

6. The method of claim 1 wherein the acidic aluminum salt comprises a mixture of aluminum sulfate and aluminum nitrate.

7. The method of claim 1 wherein the acidic aluminum salt comprises a mixture of aluminum sulfate and polyaluminum chloride.

8. The method of claim 1 wherein the means for automatically dispersing liquid comprises an ammonia sensor.

9. The method of claim 1 wherein the means for automatically dispensing liquid comprises a timer.

* * * * *